US008961972B2

(12) United States Patent
Lu et al.

(10) Patent No.: US 8,961,972 B2
(45) Date of Patent: *Feb. 24, 2015

(54) ANTI-N3PGLU AMYLOID BETA PEPTIDE ANTIBODIES AND USES THEREOF

(71) Applicant: Eli Lilly and Company, Indianapolis, IN (US)

(72) Inventors: Jirong Lu, Carmel, IN (US); Ying Tang, San Diego, CA (US); Ronald Bradley Demattos, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/039,113

(22) Filed: Sep. 27, 2013

(65) Prior Publication Data

US 2014/0065138 A1 Mar. 6, 2014

Related U.S. Application Data

(63) Continuation of application No. 13/810,895, filed as application No. PCT/US2011/046994 on Aug. 9, 2011, now Pat. No. 8,679,498.

(60) Provisional application No. 61/373,026, filed on Aug. 12, 2010.

(51) Int. Cl.
*C07K 16/18* (2006.01)
*A61K 39/395* (2006.01)
*G01N 33/577* (2006.01)
*A61K 39/00* (2006.01)

(52) U.S. Cl.
CPC ........... *C07K 16/18* (2013.01); *A61K 2039/505* (2013.01); *C07K 2317/24* (2013.01); *C07K 2317/34* (2013.01); *C07K 2317/55* (2013.01); *C07K 2317/567* (2013.01); *C07K 2317/92* (2013.01); *G01N 2800/2821* (2013.01)
USPC .................. 424/142.1; 424/141.1; 424/133.1; 530/388.15; 530/387.9

(58) Field of Classification Search
None
See application file for complete search history.

(56) References Cited

U.S. PATENT DOCUMENTS

| 7,122,374 | B1 | 10/2006 | Saido |
| 2007/0031416 | A1 | 2/2007 | Asami |
| 2008/0299111 | A1 | 12/2008 | Sergeant |
| 2010/0021478 | A1 | 1/2010 | Demuth |

FOREIGN PATENT DOCUMENTS

| WO | 2004013172 | 2/2004 |
| WO | 2006036291 A2 | 4/2006 |
| WO | 2008011348 | 1/2008 |
| WO | 2009149487 | 12/2009 |
| WO | 2010004434 | 1/2010 |
| WO | 2010009987 | 1/2010 |
| WO | 2011151076 | 12/2011 |

OTHER PUBLICATIONS

Oliver Wirths, et al., "Pyroglutamate Abeta pathology in APP/PS1K1 mice, sporadic and familial Alzheimer's disease cases", Journal of Neural Transmission, (2009), vol. 117(1), pp. 85-96.
Donna Wilcock, et al., Passive immunotherapy against Abeta in aged APP-transgenic mice reverses cognitive deficits and depletes parenchymal amyloid deposits in spite of increased vascular amyloid and microhemorrhage:, Journal of Neuroinflammation, (2004), vol. 1(1), p. 24.
Oliver Wirths, et al., "Identification of low molecular weight pyroglutamate Abeta oligomers in Alzheimer disease: a novel tool for therapy and diagnosis", Journal of Biological Chemistry, (2010), vol. 285(53), pp. 41517-41524.
David Brody, et al., "Active and passive immunotherapy for neurodegenerative disorders", Annual Review of Neuroscience, (2008), vol. 31, pp. 175-193.
Frederique Bard, et al., "Epitope and isotype specificities of antibodies to [beta]-amyloid peptide for protection against Alzheimer's disease-like neuropathy", Proc Natl Acad Science, (2003), vol. 100(4), pp. 2023-2028.
F. Luo, et al., "P2-304: MRI detection and time course of cerebral microhemorrhages during Abeta antibody treatment in living APP transgenic mice", Alzheimer's & Dementia: The Journal of the Alzheimer's Association, (2008), vol. 4(4), p. T461.
Margaret M. Racke, et al., "Exacerbation of cerebral amyloid angiopathy-associated microhemorrhage in amyloid precursor protein transgenic mice by immunotherapy is dependent on antibody recognition of deposited forms of amyloid beta", The Journal of Neuroscience: The Official Journal of the Socitey for Neuroscience, (2005), vol. 25(3), pp. 629-636.
T. A. Bayer, et al., "Intraneuronal Abeta as a trigger for neuron loss: Can this be translated into human pathology?", Biochemical Society Transactions, (2011), vol. 39(4), pp. 857-861.
Desikan et al., MRI measures of temporoparietal regions show differential rates of atrophy during prodromal AD. Neurology, 2008;71:819-825.
Fennema-Notestine et al., Structural MRI Blomarkers for Preclinical and Mild Alzheimer's Disease, Hum Brain Mapp. Oct. 2009; 30(10): 3238-3253.
Schroeter et al., Immunotherapy Reduces Vascular Amylold-beta in PDAPP Mice. The Journal of Neuroscience, Jul. 2, 2008, 28(27):6787-6793.
DeMattos et al., A Plaque-Specific Antibody Clears Existing beta-amyloid Plaques in Alzheimer's Disease Mice. Neuron 76, 908-920, Dec. 6, 2012, 908-920.

*Primary Examiner* — Gregory S Emch
*Assistant Examiner* — Aurora M Fontainhas
(74) *Attorney, Agent, or Firm* — Sanjay M. Jivraj

(57) ABSTRACT

The present invention provides anti-N3pGlu Aβ antibodies or antigen-binding fragment thereof. In addition, the present invention provides the use of the anti-N3pGlu Aβ antibodies or antigen-binding fragment thereof for the treatment of Alzheimer's disease.

12 Claims, No Drawings

SEQUENCE LISTING

```
<160> NUMBER OF SEQ ID NOS: 56

<210> SEQ ID NO 1
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(42)
<223> OTHER INFORMATION: This sequence represents amyloid beta 1-42

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(40)
<223> OTHER INFORMATION: This sequence represents N3pE amyloid beta
<220> FEATURE:
<221> NAME/KEY: MISC_FEATURE
<222> LOCATION: (1)..(1)
<223> OTHER INFORMATION: Xaa at position 1 = pyroglutamic acid

<400> SEQUENCE: 2

Xaa Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 3
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(16)
<223> OTHER INFORMATION: This sequence represents LCDR1-B12L/R17L/hE8L/
      R17

<400> SEQUENCE: 3
```

```
Lys Ser Ser Gln Ser Leu Leu Tyr Ser Arg Gly Lys Thr Tyr Leu Asn
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: This sequence represents LCDR2-B12L/R17L/he8L/
      CI-C7

<400> SEQUENCE: 4

Ala Val Ser Lys Leu Asp Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(9)
<223> OTHER INFORMATION: This sequence represents LCDR3-B12L/R17L/hE8L/
      R17/CI-C7

<400> SEQUENCE: 5

Val Gln Gly Thr His Tyr Pro Phe Thr
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: This sequence represents HCDR1-B12L

<400> SEQUENCE: 6

Gly Tyr Asp Phe Thr Arg Tyr Tyr Ile Asn
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: This sequence represents HCDR1-R17L/R17

<400> SEQUENCE: 7

Gly Tyr Thr Phe Thr Arg Tyr Tyr Ile Asn
1               5                   10

<210> SEQ ID NO 8
<211> LENGTH: 17
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(17)
<223> OTHER INFORMATION: This sequence represents HCDR2-B12L/R17L/R17/
      CI-C7

<400> SEQUENCE: 8

Trp Ile Asn Pro Gly Ser Gly Asn Thr Lys Tyr Asn Glu Lys Phe Lys
1               5                   10                  15

Gly

<210> SEQ ID NO 9
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: This sequence represents HCDR3-B12L

<400> SEQUENCE: 9

Glu Gly Ile Thr Val Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: This sequence represents HCDR3-R17L/R17

<400> SEQUENCE: 10

Glu Gly Thr Thr Val Tyr
1               5

<210> SEQ ID NO 11
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(112)
<223> OTHER INFORMATION: This sequence represents LCVR-B12L/R17L/hE8L

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
```

```
                    85                  90                  95

Thr His Tyr Pro Phe Thr Phe Gly Gln Gly Thr Lys Leu Glu Ile Lys
                100                 105                 110

<210> SEQ ID NO 12
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(115)
<223> OTHER INFORMATION: This sequence represents HCVR-B12L

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
                20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Val Tyr Trp Gly Gln Gly Thr Thr Val Thr
            100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(115)
<223> OTHER INFORMATION: This sequence represents HCVR-R17L

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
                20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
            100                 105                 110

Val Ser Ser
```

<210> SEQ ID NO 14
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(219)
<223> OTHER INFORMATION: This sequence represents LC-B12L/R17L

<400> SEQUENCE: 14

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(444)
<223> OTHER INFORMATION: This sequence represents HC-B12L

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met

```
            35                  40                  45
Gly Trp Ile Asn Pro Gly Ser Gly Asn Thr Lys Tyr Asn Glu Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Ile Thr Val Tyr Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 16
```

```
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(444)
<223> OTHER INFORMATION: This sequence represents HC-R17L

<400> SEQUENCE: 16
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys

```
                  355                 360                 365
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 17
<211> LENGTH: 336
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(336)
<223> OTHER INFORMATION: This sequence represents LCVR DNA-B12L/R17L

<400> SEQUENCE: 17
gatattgtga tgactcagac tccactctcc ctgtccgtca cccctggaca gccggcctcc      60
atctcctgca agtcaagtca gagcctctta tatagtcgcg gaaaaaccta tttgaattgg     120
ctcctgcaga agccaggcca atctccacag ctcctaattt atgcggtgtc taaactggac     180
tctggggtcc cagacagatt cagcggcagt gggtcaggca cagatttcac actgaaaatc     240
agcagggtgg aggccgaaga tgttggggtt tattactgcg tgcaaggtac acattccca     300 ttcacgtttg gccaagggac caagctggag atcaaa                              336

<210> SEQ ID NO 18
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(345)
<223> OTHER INFORMATION: This sequence represents HCVR DNA-B12L

<400> SEQUENCE: 18
caggtgcagc tggtgcagtc tggggctgag gtgaagaagc ctgggtcctc agtgaaggtt      60
tcctgcaagg catctggtta cgacttcact agatactata aaactgggt gcgacaggcc     120 cctggacaag gcttgagtg gatgggatgg attaatcctg aagcggtaa tactaagtac     180 aatgagaaat tcaagggcag agtcaccatt accgcggacg aatccacgag cacagcctac     240
atggagctga gcagcctgag atctgaggac acggccgtgt attactgtgc gagagaaggc     300
atcacggtct actggggcca aggaccacg gtcaccgtct cctca                     345

<210> SEQ ID NO 19
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(345)
```

<223> OTHER INFORMATION: This sequence represents HCVR DNA-R17L

<400> SEQUENCE: 19

```
caggtgcagc tggtgcagtc tggggctgag gtgaagaagc ctgggtcctc agtgaaggtt    60
tcctgcaagg catctggtta caccttcact agatattata taaactgggt gcgacaggcc   120
cctggacaag ggcttgagtg gatgggatgg attaatcctg gaagcggtaa tactaagtac   180
aatgagaaat tcaagggcag agtcaccatt accgcggacg aatccacgag cacagcctac   240
atggagctga gcagcctgag atctgaggac acggccgtgt attactgtgc gagagaaggc   300
acaacggtct actggggcca aggaccacg gtcaccgtct cctca                   345
```

<210> SEQ ID NO 20
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(112)
<223> OTHER INFORMATION: This sequence represents LCVR-mE8

<400> SEQUENCE: 20

```
Asn Ile Val Leu Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Tyr Ser
                20                  25                  30

Arg Gly Lys Thr Tyr Leu Asn Trp Leu Leu Gln Arg Pro Gly Gln Ser
            35                  40                  45

Pro Lys Arg Leu Ile Tyr Ala Val Ser Lys Leu Asp Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Tyr Pro Phe Thr Phe Gly Ser Gly Thr Lys Leu Glu Ile Lys
            100                 105                 110
```

<210> SEQ ID NO 21
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(115)
<223> OTHER INFORMATION: This sequence represents HCVR-mE8

<400> SEQUENCE: 21

```
Glu Val Gln Leu Leu Glu Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Gly Trp Ile Asn Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80
```

```
Met Gln Leu Ser Ser Leu Thr Ser Glu Asp Ser Ala Val Tyr Phe Cys
                85                  90                  95

Thr Arg Glu Gly Glu Thr Val Tyr Trp Gly Gln Gly Thr Thr Leu Thr
            100                 105                 110

Val Ser Ser
        115

<210> SEQ ID NO 22
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(219)
<223> OTHER INFORMATION: This sequence represents LC-mE8 and mE8c

<400> SEQUENCE: 22

Asn Ile Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Arg Pro Gly Gln Ser
        35                  40                  45

Pro Lys Arg Leu Ile Tyr Ala Val Ser Lys Leu Asp Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Tyr Pro Phe Thr Phe Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 23
<211> LENGTH: 439
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(439)
<223> OTHER INFORMATION: This sequence represents HC-mE8

<400> SEQUENCE: 23
```

```
Glu Val Gln Leu Leu Glu Ser Gly Pro Glu Val Lys Pro Gly Ala
 1               5                  10                  15

Ser Val Lys Ile Ser Cys Lys Ala Ser Gly Tyr Thr Phe Thr Asp Tyr
             20                  25                  30

Tyr Ile Asn Trp Val Lys Gln Arg Pro Gly Gln Gly Leu Glu Trp Ile
             35                  40                  45

Gly Trp Ile Asn Pro Gly Ser Gly Asn Thr Lys Tyr Asn Glu Lys Phe
 50                  55                  60

Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Phe Cys
                 85                  90                  95

Thr Arg Glu Gly Glu Thr Val Tyr Trp Gly Gln Gly Thr Thr Leu Thr
                100                 105                 110

Val Ser Ser Ala Lys Thr Thr Pro Pro Ser Val Tyr Pro Leu Ala Pro
             115                 120                 125

Gly Ser Ala Ala Gln Thr Asn Ser Met Val Thr Leu Gly Cys Leu Val
 130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
                180                 185                 190

Glu Thr Val Thr Cys Asn Val Ala His Pro Ala Ser Ser Thr Lys Val
                195                 200                 205

Asp Lys Lys Ile Val Pro Arg Asp Cys Gly Cys Lys Pro Cys Ile Cys
210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
                260                 265                 270

Asp Val Glu Val His Thr Ala Gln Thr Gln Pro Arg Glu Glu Gln Phe
                275                 280                 285

Asn Ser Thr Phe Arg Ser Val Ser Glu Leu Pro Ile Met His Gln Asp
                290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
                340                 345                 350

Asp Lys Val Ser Leu Thr Cys Met Ile Thr Asp Phe Phe Pro Glu Asp
                355                 360                 365

Ile Thr Val Glu Trp Gln Trp Asn Gly Gln Pro Ala Glu Asn Tyr Lys
                370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415
```

```
Cys Ser Val Leu His Glu Gly Leu His Asn His His Thr Glu Lys Ser
            420                 425                 430
Leu Ser His Ser Pro Gly Lys
            435

<210> SEQ ID NO 24
<211> LENGTH: 445
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(445)
<223> OTHER INFORMATION: This sequence represents HC-mE8c

<400> SEQUENCE: 24

Glu Val Gln Leu Leu Glu Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
            35                  40                  45

Gly Trp Ile Asn Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Glu Gly Glu Thr Val Tyr Trp Gly Gln Gly Thr Thr Leu Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320
```

```
Val Asn Asn Lys Asp Leu Pro Ala Pro Ile Glu Arg Thr Ile Ser Lys
            325                 330                 335

Pro Lys Gly Ser Val Arg Ala Pro Gln Val Tyr Val Leu Pro Pro Pro
        340                 345                 350

Glu Glu Glu Met Thr Lys Lys Gln Val Thr Leu Thr Cys Met Val Thr
            355                 360                 365

Asp Phe Met Pro Glu Asp Ile Tyr Val Glu Trp Thr Asn Asn Gly Lys
        370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Gln Lys Lys Asn Trp Val
            405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445

<210> SEQ ID NO 25
<211> LENGTH: 14
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: This seqence represents pE3-16
<220> FEATURE:
<221> NAME/KEY: MISC_FEATURE
<222> LOCATION: (1)..(1)
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 25

Xaa Phe Arg His Asp Ser Gly Tyr Glu Val His His Gln Lys
1               5                   10

<210> SEQ ID NO 26
<211> LENGTH: 14
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: This sequence represents E3-16
<220> FEATURE:
<221> NAME/KEY: MOD_RES
<222> LOCATION: (14)..(14)
<223> OTHER INFORMATION: Lys at position 14 is modified with biotin

<400> SEQUENCE: 26

Glu Phe Arg His Asp Ser Gly Tyr Glu Val His His Gln Lys
1               5                   10

<210> SEQ ID NO 27
<211> LENGTH: 14
<212> TYPE: PRT
<213> ORGANISM: artificial sequence
<220> FEATURE:
<223> OTHER INFORMATION: Synthetic construct
<220> FEATURE:
```

-continued

```
<221> NAME/KEY: MISC_FEATURE
<222> LOCATION: (1)..(14)
<223> OTHER INFORMATION: This sequence represents pEG4
<220> FEATURE:
<221> NAME/KEY: MISC_FEATURE
<222> LOCATION: (1)..(1)
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 27

Xaa Gly Arg His Asp Ser Gly Tyr Glu Val His His Gln Lys
1               5                   10

<210> SEQ ID NO 28
<211> LENGTH: 14
<212> TYPE: PRT
<213> ORGANISM: rattus rattus
<220> FEATURE:
<221> NAME/KEY: MISC_FEATURE
<222> LOCATION: (1)..(14)
<223> OTHER INFORMATION: This sequence represents mpE3-16
<220> FEATURE:
<221> NAME/KEY: MISC_FEATURE
<222> LOCATION: (1)..(1)
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 28

Xaa Phe Gly His Asp Ser Gly Phe Glu Val His His Gln Lys
1               5                   10

<210> SEQ ID NO 29
<211> LENGTH: 14
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: This sequence represents pEG6
<220> FEATURE:
<221> NAME/KEY: MISC_FEATURE
<222> LOCATION: (1)..(1)
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 29

Xaa Phe Arg Gly Asp Ser Gly Tyr Glu Val His His Gln Lys
1               5                   10

<210> SEQ ID NO 30
<211> LENGTH: 14
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: This sequence represents pEG7
<220> FEATURE:
<221> NAME/KEY: MISC_FEATURE
<222> LOCATION: (1)..(1)
```

```
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 30

Xaa Phe Arg His Gly Ser Gly Tyr Glu Val His His Gln Lys
1               5                   10

<210> SEQ ID NO 31
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(112)
<223> OTHER INFORMATION: This sequence represents LCVR-hE8-C6

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Tyr Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 32
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(115)
<223> OTHER INFORMATION: This sequence represents HCVR-hE8-C6

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Thr Val Tyr Trp Gly Gln Gly Thr Thr Val Thr
```

Val Ser Ser
    115

<210> SEQ ID NO 33
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(219)
<223> OTHER INFORMATION: This sequence represents LC-hE8-C6

<400> SEQUENCE: 33

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Tyr Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Gln Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 34
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(444)
<223> OTHER INFORMATION: This sequence represents HC-hE8-C6

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr

```
                    20                  25                  30
Tyr Ile Asn Trp Val Arg Gln Ala Pro Gly Gln Gly Leu Glu Trp Met
                35                  40                  45
Gly Trp Ile Asn Pro Gly Ser Gly Asn Thr Lys Tyr Asn Glu Lys Phe
         50                  55                  60
Lys Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Gly Glu Thr Val Tyr Trp Gly Gln Gly Thr Thr Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
    275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
            435                 440
```

<210> SEQ ID NO 35
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: This sequence represents LCDR2-R17

<400> SEQUENCE: 35

Ala Val Ser Lys Leu Gly Ser
1               5

<210> SEQ ID NO 36
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(112)
<223> OTHER INFORMATION: This sequence represents LCVR-R17

<400> SEQUENCE: 36

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Tyr Leu Gln Lys Pro Gly Gln Ser
        35                  40                  45

Pro Gln Leu Leu Ile Tyr Ala Val Ser Lys Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 37
<211> LENGTH: 14
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: This sequence represents pEG8
<220> FEATURE:
<221> NAME/KEY: MISC_FEATURE
<222> LOCATION: (1)..(1)
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 37

Xaa Phe Arg His Asp Gly Gly Tyr Glu Val His His Gln Lys
1               5                   10

```
<210> SEQ ID NO 38
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(219)
<223> OTHER INFORMATION: This sequence represents LC-R17

<400> SEQUENCE: 38

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Tyr Leu Gln Lys Pro Gly Gln Ser
        35                  40                  45

Pro Gln Leu Leu Ile Tyr Ala Val Ser Lys Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 39
<211> LENGTH: 14
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: This sequence represents pEF10
<220> FEATURE:
<221> NAME/KEY: MISC_FEATURE
<222> LOCATION: (1)..(1)
<223> OTHER INFORMATION: Xaa at position 1 = pyroglutamic acid
<220> FEATURE:
<221> NAME/KEY: MOD_RES
<222> LOCATION: (14)..(14)
<223> OTHER INFORMATION: Lys at position 14 is modified with biotin

<400> SEQUENCE: 39

Xaa Phe Arg His Asp Ser Gly Phe Glu Val His His Gln Lys
1               5                   10
```

<210> SEQ ID NO 40
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: This sequence represents HCDR1-hE8L/CI-C7

<400> SEQUENCE: 40

Gly Tyr Thr Phe Thr Asp Tyr Tyr Ile Asn
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: This sequence represents HCDR3-hE8L

<400> SEQUENCE: 41

Glu Gly Glu Thr Val Tyr
1               5

<210> SEQ ID NO 42
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(115)
<223> OTHER INFORMATION: This sequence represents HCVR-hE8L

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Thr Val Tyr Trp Gly Gln Gly Thr Thr Val Thr
            100                 105                 110

Val Ser Ser
        115

<210> SEQ ID NO 43
<211> LENGTH: 1332
<212> TYPE: DNA
<213> ORGANISM: artificial sequence
<220> FEATURE:

```
<223> OTHER INFORMATION: Synthetic construct
<220> FEATURE:
<221> NAME/KEY: misc_feature
<222> LOCATION: (1)..(1332)
<223> OTHER INFORMATION: This sequence represents HC DNA-R17L
<220> FEATURE:
<221> NAME/KEY: misc_feature
<222> LOCATION: (1)..(1332)
<223> OTHER INFORMATION: This sequence represents HC DNA-R17L

<400> SEQUENCE: 43
caggtgcagc tggtgcagtc tggggctgag gtgaagaagc ctgggtcctc agtgaaggtt      60
tcctgcaagg catctggtta caccttcact agatattata taaactgggt gcgacaggcc     120
cctggacaag ggcttgagtg gatgggatgg attaatcctg aagcggtaa tactaagtac     180
aatgagaaat tcaagggcag agtcaccatt accgcggacg aatccacgag cacagcctac     240
atggagctga gcagcctgag atctgaggac acggccgtgt attactgtgc gagagaaggc     300
acaacggtct actggggcca aggaccacg gtcaccgtct cctcagcctc caccaagggc     360
ccatcggtct tccccgctag cacctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttccgggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg acgagctgac caagaaccag    1080
gtcagcctga cctgcctggt caaaggcttc tatcccagcg acatcgccgt ggagtgggag    1140
agcaatgggc agccggagaa caactacaag accacgcccc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                        1332

<210> SEQ ID NO 44
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(444)
<223> OTHER INFORMATION: This sequence represents HC-hE8L

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
```

```
            35                  40                  45
Gly Trp Ile Asn Pro Gly Ser Gly Asn Thr Lys Tyr Asn Glu Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Glu Thr Val Tyr Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 45
```

```
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(16)
<223> OTHER INFORMATION: This sequence represents LCDR1-CI-C7

<400> SEQUENCE: 45

Lys Ser Thr Arg Ser Leu Leu Tyr Ser Arg Ser Lys Thr Tyr Leu Asn
1               5                   10                  15

<210> SEQ ID NO 46
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: This sequence represents HCDR3-CI-C7

<400> SEQUENCE: 46

Glu Gly Val Thr Val Tyr
1               5

<210> SEQ ID NO 47
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(112)
<223> OTHER INFORMATION: This sequence represents LCVR-CI-C7

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ser Thr Arg Ser Leu Leu Tyr Ser
            20                  25                  30

Arg Ser Lys Thr Tyr Leu Asn Trp Tyr Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Val Gln Gly
                85                  90                  95

Thr His Tyr Pro Phe Thr Phe Gly Gly Gly Thr Lys Val Glu Ile Lys
            100                 105                 110

<210> SEQ ID NO 48
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(115)
<223> OTHER INFORMATION: This sequence represents HCVR-CI-C7
```

<400> SEQUENCE: 48

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asp Tyr
            20                  25                  30

Tyr Ile Asn Trp Val Arg Gln Met Pro Gly Lys Gly Leu Glu Trp Met
        35                  40                  45

Gly Trp Ile Asn Pro Gly Ser Gly Asn Thr Lys Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Val Thr Val Tyr Trp Gly Gln Gly Thr Leu Val Thr
            100                 105                 110

Val Ser Ser
        115

<210> SEQ ID NO 49
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(219)
<223> OTHER INFORMATION: This sequence represents LC-CI-C7

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ser Thr Arg Ser Leu Leu Tyr Ser
            20                  25                  30

Arg Ser Lys Thr Tyr Leu Asn Trp Tyr Gln Gln Lys Pro Gly Lys Ala
        35                  40                  45

Pro Lys Leu Leu Ile Tyr Ala Val Ser Lys Leu Asp Ser Gly Val Pro
50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Val Gln Gly
                85                  90                  95

Thr His Tyr Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

```
Pro Val Thr Lys Ser Phe Asn Arg Gly Glu Cys
    210                 215
```

<210> SEQ ID NO 50
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(444)
<223> OTHER INFORMATION: This sequence represents HC-CI-C7

<400> SEQUENCE: 50

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asp Tyr
            20                  25                  30

Tyr Ile Asn Trp Val Arg Gln Met Pro Gly Lys Gly Leu Glu Trp Met
        35                  40                  45

Gly Trp Ile Asn Pro Gly Ser Gly Asn Thr Lys Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Val Thr Val Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335
```

```
Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 51
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(16)
<223> OTHER INFORMATION: This sequence represents LCDR1 consensus
<220> FEATURE:
<221> NAME/KEY: MISC_FEATURE
<222> LOCATION: (3)..(3)
<223> OTHER INFORMATION: X at position 3 = S or T
<220> FEATURE:
<221> NAME/KEY: MISC_FEATURE
<222> LOCATION: (4)..(4)
<223> OTHER INFORMATION: X at position 4 = Q or R
<220> FEATURE:
<221> NAME/KEY: MISC_FEATURE
<222> LOCATION: (11)..(11)
<223> OTHER INFORMATION: X at position 11 = G or S

<400> SEQUENCE: 51

Lys Ser Xaa Xaa Ser Leu Leu Tyr Ser Arg Xaa Lys Thr Tyr Leu Asn
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: This sequence represents LCDR2 consensus
<220> FEATURE:
<221> NAME/KEY: MISC_FEATURE
<222> LOCATION: (6)..(6)
<223> OTHER INFORMATION: X at position 6 = D or G

<400> SEQUENCE: 52

Ala Val Ser Lys Leu Xaa Ser
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(10)
<223> OTHER INFORMATION: This sequence represents HCDR1 consensus
<220> FEATURE:
<221> NAME/KEY: MISC_FEATURE
<222> LOCATION: (3)..(3)
<223> OTHER INFORMATION: X at position 3 = D or T
<220> FEATURE:
<221> NAME/KEY: MISC_FEATURE
<222> LOCATION: (6)..(6)
<223> OTHER INFORMATION: X at position 6 = R or D

<400> SEQUENCE: 53

Gly Tyr Xaa Phe Thr Xaa Tyr Tyr Ile Asn
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: This sequence represents HCDR3 consensus
<220> FEATURE:
<221> NAME/KEY: MISC_FEATURE
<222> LOCATION: (3)..(3)
<223> OTHER INFORMATION: X at position 3 = I, T, E or V

<400> SEQUENCE: 54

Glu Gly Xaa Thr Val Tyr
1               5

<210> SEQ ID NO 55
<211> LENGTH: 657
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(657)
<223> OTHER INFORMATION: This sequence represents LC DNA-B12L/R17L
<220> FEATURE:
<221> NAME/KEY: misc_feature
<222> LOCATION: (1)..(657)
<223> OTHER INFORMATION: This sequence represents LC DNA-B12L/R17L

<400> SEQUENCE: 55
gatattgtga tgactcagac tccactctcc ctgtccgtca cccctggaca gccggcctcc      60
atctcctgca agtcaagtca gagcctctta tatagtcgcg gaaaaaccta tttgaattgg     120
ctcctgcaga agccaggcca atctccacag ctcctaattt atgcggtgtc taaactggac     180
tctggggtcc cagacagatt cagcggcagt gggtcaggca cagatttcac actgaaaatc     240
agcagggtgg aggccgaaga tgttgggggtt tattactgcg tgcaaggtac acattaccca     300
ttcacgtttg gccaagggac caagctggag atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgc       657
```

```
<210> SEQ ID NO 56
<211> LENGTH: 1332
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1332)
<223> OTHER INFORMATION: This sequence represents HC DNA-B12L

<400> SEQUENCE: 56
caggtgcagc tggtgcagtc tggggctgag gtgaagaagc ctgggtcctc agtgaaggtt      60
tcctgcaagg catctggtta cgacttcact agatactata taaactgggt gcgacaggcc     120
cctggacaag ggcttgagtg gatgggatgg attaatcctg gaagcggtaa tactaagtac     180
aatgagaaat tcaagggcag agtcaccatt accgcggacg aatccacgag cacagcctac     240
atggagctga gcagcctgag atctgaggac acggccgtgt attactgtgc gagagaaggc     300
atcacggtct actgggccca agggaccacg gtcaccgtct cctcagcctc caccaagggc     360
ccatcggtct tccccctagc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcctgg ggggaccgtc agtcttcctc     720
ttccccccaa acccaaggac accctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca agccctccag ccccatc gagaaaacca tctccaaagc caaagggcag    1020
ccccgagaac cacaggtgta caccctgccc ccatcccggg acgagctgac caagaaccag    1080
gtcagcctga cctgcctggt caaaggcttc tatcccagcg acatcgccgt ggagtgggag    1140
agcaatgggc agccggagaa caactacaag accacgcccc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                        1332
```

US 8,961,972 B2

ANTI-N3PGLU AMYLOID BETA PEPTIDE ANTIBODIES AND USES THEREOF

This application is a continuation of patent application U.S. Ser. No. 13/810,895 filed Jan. 18, 2013, which claims priority to PCT patent application PCT/US2011/046994, filed Aug. 9, 2011, which claims the priority of U.S. provisional application 61/373,026, filed Aug. 12, 2010. The contents of each of these applications are incorporated herein by reference.

The present invention relates to antibodies that selectively bind N3pGlu Amyloid Beta peptide and their use in treating diseases related to Amyloid Beta (Aβ, also referred to as Abeta) peptide.

The Aβ peptide in circulating form is composed of 38-43 amino acids (mostly 38, 40 or 42 amino acids) resulting from the cleavage of a precursor protein, amyloid precursor protein (APP). Conversion of Aβ from soluble to insoluble forms having high β-sheet content and the deposition of these insoluble forms as neuritic and cerebrovascular plaques in the brain has been associated with a number of conditions and diseases, including Alzheimer's disease (AD), Down's syndrome, and cerebral amyloid angiopathy (CAA).

The deposits found in plaques are comprised mainly of a heterogeneous mixture of Aβ peptides. N3pGlu Aβ, also referred to as N3pE or $A\beta_{p3-42}$, is a truncated form of the Aβ peptide found only in plaques. N3pGlu Aβ lacks the first two amino acid residues at the N-terminus of Aβ and has a pyroglutamate which was derived from the glutamic acid at the third amino acid position. Although N3pGlu Aβ peptide is a minor component of the deposited Aβ in the brain, studies have demonstrated that N3pGlu Aβ peptide has aggressive aggregation properties and accumulates early in the deposition cascade.

While polyclonal and monoclonal antibodies that target the N3pGlu Aβ peptide have been previously described (U.S. Pat. No. 7,122,374 and WO2010/009987), there is still a need for high affinity anti-N3pGlu Aβ monoclonal antibodies to engage the target in vivo (i.e. plaque binding) and subsequently lower plaque levels. In addition, given that amino-terminal and carboxyl-terminal anti-Aβ antibodies lead to an increase in cerebral amyloid angiopathy (CAA) related microhemorrhage, there is a need for anti-N3pGlu Aβ antibodies that do not result in an increase in microhemorrhage even though chronic treatment results in a significant reduction of deposited plaque.

The antibodies within the scope of the present invention are therapeutically useful N3pGlu Aβ peptide antagonists possessing a number of desirable properties. The present antibodies bind human N3pGlu Aβ peptide with high affinity and exhibit dose-dependent in vivo plaque lowering without an increase in cerebral amyloid angiopathy (CAA) related microhemorrhage.

The present invention provides a human engineered anti-N3pGlu Aβ antibody, or antigen-binding fragment thereof that has a Kd at 25° C. of less than $1 \times 10^{-9}$ M for human N3pGlu Aβ peptide. In a preferred embodiment, the present invention provides a human engineered anti-N3pGlu Aβ antibody, or antigen-binding fragment thereof that has a Kd at 25° C. of less than $9 \times 10^{-10}$ M for human N3pGlu Aβ peptide. In another preferred embodiment, the present invention provides a human engineered anti-N3pGlu Aβ antibody, or antigen-binding fragment thereof that has a Kd at 25° C. of less than $7 \times 10^{-10}$ M for human N3pGlu Aβ peptide. In another preferred embodiment, the present invention provides a human engineered anti-N3pGlu Aβ antibody, or antigen-binding fragment thereof that has a Kd at 25° C. between $9 \times 10^{-10}$ M and $1 \times 10^{-10}$ M for human N3pGlu Aβ peptide. In another preferred embodiment, the present invention provides a anti-N3pGlu Aβ antibody, or antigen-binding fragment thereof that has a Kd at 25° C. between $9 \times 10^{-10}$ M and $1 \times 10^{-10}$ M for human N3pGlu Aβ peptide.

The present invention further provides a human engineered anti-N3pGlu Aβ antibody, or antigen-binding fragment thereof that has a Kd at 25° C. of less than $1 \times 10^{-9}$ M, or less than $9 \times 10^{-10}$ M, or less than $7 \times 10^{-10}$ M, or between $9 \times 10^{-10}$ M and $1 \times 10^{-10}$ M for human N3pGlu Aβ peptide and lowers plaque in vivo. In a further preferred embodiment, the present invention provides a human engineered anti-N3pGlu Aβ antibody, or antigen-binding fragment thereof that has a Kd at 25° C. of less than $1 \times 10^{-9}$ M, or less than $9 \times 10^{-10}$ M, or less than $7 \times 10^{-10}$ M, or between $9 \times 10^{-10}$ M and $1 \times 10^{-10}$ M for human N3pGlu Aβ peptide and lowers plague in vivo without increasing CAA related microhemorrhage.

The present invention also provides a human engineered anti-N3pGlu Aβ antibody or antigen-binding fragment thereof comprising an LCVR and an HCVR wherein LCDR1 is $KSX_1X_2SLLYSRX_3KTYLN$ (SEQ ID NO: 51), LCDR2 is $AVSKLX_4S$ (SEQ ID NO: 52), LCDR3 is VQGTHYPFT (SEQ ID NO: 5) and HCDR1 is $GYX_5FTX_6YYIN$ (SEQ ID NO: 53), HCDR2 is WINPGSGNTKYNEKFKG (SEQ ID NO: 8), and HCDR3 is $EGX_7TVY$ (SEQ ID NO: 54), wherein $X_1$ is S or T; $X_2$ is Q or R, $X_3$ is G or S, $X_4$ is D or G, $X_5$ is D or T, $X_6$ is R or D, and $X_7$ is I, T, E, or V.

The present invention provides a human engineered anti-N3pGlu Aβ antibody, or antigen-binding fragment thereof comprising a light chain variable region (LCVR) and a heavy chain variable region (HCVR), wherein said LCVR comprises LCDR1, LCDR2, LCDR3 polypeptides and HCVR comprises HCDR1, HCDR2, HCDR3 polypeptides which are selected from the group consisting of:

a) LCDR1 is KSSQSLLYSRGKTYLN (SEQ ID NO: 3), LCDR2 is AVSKEDS (SEQ ID NO: 4), LCDR3 is VQGTHYPFT (SEQ ID NO: 5), HCDR1 is GYDFTRYYIN (SEQ ID NO: 6). HCDR2 is WINPGSGNTKYNEKEKG (SEQ ID NO: 8), and HCDR3 is EGITVY (SEQ ID NO: 9);

b) LCDR1 is KSSQSLLYSRGKTYEN (SEQ ID NO: 3). ECDR2 is AVSKEDS (SEQ ID NO: 4). LCDR3 is VQGTHYPFT (SRQ ID NO: 5), HCDR1 is GYTFTRYYIN (SEQ ID NO: 7). IICDR2 is WINPGSGNTKYNEKFKG (SEQ ID NO: 8). and HCDR3 is EGTTVY (SEQ ID NO: 10);

c) LCDR1 is KSSQSLLYSRGKTYLN (SEQ ID NO: 3), LCDR2 is AVSKLDS (SEQ ID NO: 4). LCDR3 is VQGTHYPFT (SEQ ID NO: 5). HCDR1 is GYTFTDYYIN (SEQ ID NO: 40), HCDR2 is WINPGSGNTKYNEKFKG (SEQ ID NO: 8), and HCDR3 is EGETVY (SEQ ID NO: 41);

d) LCDR1 is KSSQSLLYSRGKTYEN (SEQ ID NO: 3), ECDR2 is AVSKLGS (SEQ ID NO: 35). LCDR3 is VQGTHYPFT (SEQ ID NO: 5), IICDR1 is GYTITRYYIN (SEQ ID NO: 7). HCDR2 is WINPGSGNTKYNEKFKG (SEQ ID NO: 8), and HCDR3 is EGTTVY (SEQ ID NO: 10); and e) LCDR1 is KSTRSLLYSRSKTYLN (SEQ ID NO: 45), LCDR2 is AVSKLDS (SEQ ID NO: 4), LCDR3 is VQGTHYPFT (SEQ ID NO: 5), IICDR1 is GYTITDYYIN (SEQ ID NO: 40), HCDR2 is WINPGSGNTKYNEKFKG (SEQ ID NO: 8). and HCDR3 is KGVTVY (SEQ ID NO: 46).

In an embodiment, the present invention provides a human engineered anti-N3pGlu Aβ antibody or antigen-binding fragment thereof comprising an LCVR and an HCVR wherein LCDR1 is SEQ ID NO: 3, LCDR2 is SEQ ID NO: 4, LCDR3 is SEQ ID NO: 5, HCDR1 is SEQ ID NO: 6, HCDR2 is SEQ ID NO: 8, and HCDR3 is SEQ ID NO: 9. In an embodiment, the present invention provides a human engineered Anti-N3pGlu Aβ antibody or antigen-binding fragment thereof comprising an LCVR and an HCVR wherein LCDR1 is SEQ ID NO: 3, LCDR2 is SEQ ID NO: 4, LCDR3 is SEQ ID NO: 5, HCDR1 is SEQ ID NO: 7, HCDR2 is SEQ ID NO: 8, and HCDR3 is SEQ ID NO: 10. In a preferred embodiment, the present invention provides a human engineered Anti-N3pGlu Aβ antibody or antigen-binding fragment thereof comprising an LCVR and an HCVR wherein LCDR1 is SEQ ID NO: 3, LCDR2 is SEQ ID NO: 4, LCDR3 is SEQ ID NO: 5, HCDR1 is SEQ ID NO: 40, HCDR2 is SEQ ID NO: 8, and HCDR3 is SEQ ID NO: 41. In a preferred embodiment, the present invention provides a human engineered anti-N3pGlu Aβ antibody or antigen-binding fragment thereof comprising an LCVR and an HCVR wherein LCDR1 is SEQ ID NO: 3, LCDR2 is SEQ ID NO: 35, LCDR3 is SEQ ID NO: 5, HCDR1 is SEQ ID NO: 7, HCDR2 is SEQ ID NO: 8, and HCDR3 is SEQ ID NO: 10. In a preferred embodiment, the present invention provides a human engineered anti-N3pGlu Aβ antibody or antigen-binding fragment thereof comprising an LCVR and an HCVR wherein LCDR1 is SEQ ID NO: 45, LCDR2 is SEQ ID NO: 4, LCDR3 is SEQ ID NO: 5, HCDR1 is SEQ ID NO: 40, HCDR2 is SEQ ID NO: 8, and HCDR3 is SEQ ID NO: 46.

In another embodiment, the present invention provides a human engineered anti-N3pGlu Aβ antibody, or antigen-binding fragment thereof comprising a light chain variable region (LCVR) and a heavy chain variable region (HCVR), wherein said LCVR and HCVR are polypeptides selected from the group consisting of:
 a. LCVR of SEQ ID NO: 11 and HCVR of SEQ ID NO: 12;
 b. LCVR of SEQ ID NO: 11 and HCVR of SEQ ID NO: 13;
 c. LCVR of SEQ ID NO: 11 and HCVR of SEQ ID NO: 42;
 d. LCVR of SEQ ID NO: 36 and HCVR of SEQ ID NO: 37; and
 e. LCVR of SEQ ID NO: 47 and HCVR of SEQ ID NO: 48.

In an embodiment, the present invention provides an anti-N3pGlu Aβ monoclonal antibody or antigen-binding fragment thereof comprising an LCVR of SEQ ID NO: 11 and an HCVR of SEQ ID NO: 12. In an embodiment, the present invention provides an anti-N3pGlu Aβ monoclonal antibody or antigen-binding fragment thereof comprising an LCVR of SEQ ID NO: 11 and an HCVR of SEQ ID NO: 13. In an embodiment, the present invention provides an anti-N3pGlu Aβ monoclonal antibody or antigen-binding fragment thereof comprising an LCVR of SEQ ID NO: 11 and an HCVR of SEQ ID NO: 42. In a preferred embodiment, the present invention provides an anti-N3pGlu Aβ monoclonal antibody or antigen-binding fragment thereof comprising an LCVR of SEQ ID NO: 36 and an HCVR of SEQ ID NO: 37. In a preferred embodiment, the present invention provides an anti-N3pGlu Aβ monoclonal antibody or antigen-binding fragment thereof comprising an LCVR of SEQ ID NO: 47 and an HCVR of SEQ ID NO: 48.

The present invention also provides an anti-N3pGlu Aβ monoclonal antibody comprising a light chain (LC) and a heavy chain (HC), wherein the LC and HC polypeptides are selected from the group consisting of:
 a) LC of SEQ ID NO: 14 and HC of SEQ ID NO: 15;
 b) LC of SEQ ID NO: 14 and HC of SEQ ID NO: 16;
 c) LC of SEQ ID NO: 14 and HC of SEQ ID NO: 44;
 d) LC of SEQ ID NO: 38 and HC of SEQ ID NO: 39; and
 e) LC of SEQ ID NO: 49 and HC of SEQ ID NO: 50.

In an embodiment, the present invention provides an anti-N3pGlu Aβ monoclonal antibody or antigen-binding fragment thereof comprising an LC of SEQ ID NO: 14 and an HC of SEQ ID NO: 15. In an embodiment, the present invention provides an anti-N3pGlu Aβ monoclonal antibody or antigen-binding fragment thereof comprising an LC of SEQ ID NO: 14 and an HC of SEQ ID NO: 16. In an embodiment, the present invention provides an anti-N3pGlu Aβ monoclonal antibody or antigen-binding fragment thereof comprising an LC of SEQ ID NO: 14 and an HC of SEQ ID NO: 44. In a preferred embodiment, the present invention provides an anti-N3pGlu Aβ monoclonal antibody or antigen-binding fragment thereof comprising an LC of SEQ ID NO: 38 and an HC of SEQ ID NO: 39. In a preferred embodiment, the present invention provides an anti-N3pGlu Aβ monoclonal antibody or antigen-binding fragment thereof comprising an LC of SEQ ID NO: 49 and an HC of SEQ ID NO: 50.

In a preferred embodiment, the anti-N3pGlu Aβ monoclonal antibody comprises two light chains and two heavy chains wherein each LC is the polypeptide of SEQ ID NO: 14 and each HC is the polypeptide of SEQ ID NO: 15. In a preferred embodiment, the anti-N3pGlu Aβ monoclonal antibody comprises two light chains and two heavy chains wherein each LC is the polypeptide of SEQ ID NO: 14 and each HC is the polypeptide of SEQ ID NO: 16. In a preferred embodiment, the anti-N3pGlu Aβ monoclonal antibody comprises two light chains and two heavy chains wherein each LC is the polypeptide of SEQ ID NO: 14 and each HC is the polypeptide of SEQ ID NO: 44. In a preferred embodiment, the anti-N3pGlu Aβ monoclonal antibody comprises two light chains and two heavy chains wherein each LC is the polypeptide of SEQ ID NO: 38 and each HC is the polypeptide of SEQ ID NO: 39. In a preferred embodiment, the anti-N3pGlu Aβ monoclonal antibody comprises two light chains and two heavy chains wherein each LC is the polypeptide of SEQ ID NO: 49 and each HC is the polypeptide of SEQ ID NO: 50.

The present invention also provides a pharmaceutical composition comprising an anti-N3pGlu Aβ monoclonal antibody of the present invention or antigen-binding fragment thereof. In a preferred embodiment, the pharmaceutical composition comprises an anti-N3pGlu Aβ monoclonal antibody of the present invention or antigen-binding fragment thereof and a pharmaceutically acceptable carrier, diluent, or excipient. In another preferred embodiment, the pharmaceutical composition additionally comprises one or more therapeutic ingredients.

In a further aspect, the present invention provides a method of treating a condition associated with Aβ peptide activity, comprising administering to a human patient in need thereof an anti-N3pGlu Aβ monoclonal antibody or antigen-binding fragment of the present invention.

In a further aspect, the present invention provides a method of treating a condition selected from a group consisting of clinical or pre-clinical Alzheimer's disease, prodromal Alzheimer's disease, Down's syndrome, and clinical or pre-clinical CAA, comprising administering to a human in need thereof an anti-N3pGlu Aβ monoclonal antibody of the present invention or antigen-binding fragment thereof. In a preferred embodiment, the present invention provides a method of treating Alzheimer's disease.

In a further aspect, the present invention provides an anti-N3pGlu Aβ monoclonal antibody or antigen-binding fragment thereof, for use in therapy. In a preferred embodiment, the present invention provides an anti-N3pGlu Aβ monoclonal antibody or antigen-binding fragment thereof, for use in the treatment of a condition selected from clinical or preclinical Alzheimer's disease, prodromal Alzheimer's disease, Down's syndrome, or clinical or pre-clinical CAA. In a more preferred embodiment, the present invention provides an anti-N3pGlu Aβ monoclonal antibody or antigen-binding fragment thereof, for use in the treatment of Alzheimer's disease. In another preferred embodiment, the present invention provides an anti-N3pGlu Aβ monoclonal antibody or antigen-binding fragment thereof, for use in the prevention of a condition selected from clinical or pre-clinical Alzheimer's disease, prodromal Alzheimer's disease, clinical or pre-clinical CAA. In a more preferred embodiment, the present invention provides an anti-N3pGlu Aβ monoclonal antibody or antigen-binding fragment thereof for use in the prevention of Alzheimer's disease.

In a further aspect, the present invention provides a use of an anti-N3pGlu Aβ monoclonal antibody or antigen-binding fragment thereof, in the manufacture of a medicament for the treatment of a condition selected from a group consisting of clinical or pre-clinical Alzheimer's disease, prodromal Alzheimer's disease, Down's syndrome, and clinical or pre-clinical CAA. In a preferred embodiment, the present invention provides a use of an anti-N3pGlu Aβ monoclonal antibody or antigen-binding fragment thereof, in the manufacture of a medicament for the treatment of Alzheimer's disease.

A full-length antibody is an immunoglobulin molecule comprising 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function.

The CDRs are interspersed with regions that are conserved, termed framework regions (FR). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with the well-known Kabat numbering convention.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, or IgG4. Each heavy chain type is characterized by a particular constant region with a sequence well known in the art.

As used herein, the term "monoclonal antibody" (Mab) refers to an antibody that is derived or isolated from a single copy or clone including, for example, any eukaryotic, prokaryotic, or phage clone, and not the method by which it is produced. Mabs of the present invention preferably exist in a homogeneous or substantially homogeneous population. Complete Mabs contain 2 heavy chains and 2 light chains. The phrase "antigen-binding fragments" includes, for example, Fab fragments, Fab' fragments, F(ab')₂ fragments, and single chain Fv fragments. Monoclonal antibodies of the present invention and antigen-binding fragments thereof can be produced, for example, by recombinant technologies, phage display technologies, synthetic technologies, e.g., CDR-grafting, or combinations of such technologies, or other technologies known in the art. For example, mice can be immunized with human Anti-N3pGlu Aβ or fragments thereof, the resulting antibodies can be recovered and purified, and determination of whether they possess binding and functional properties similar to or the same as the antibody compounds disclosed herein can be assessed by the methods disclosed essentially as described in Examples below. Antigen-binding fragments can also be prepared by conventional methods. Methods for producing and purifying antibodies and antigen-binding fragments are well known in the art and can be found, for example, in Harlow and Lane (1988) Antibodies, A Laboratory Manual, Cold Spring Harbor Laboratory Press, Cold Spring Harbor, N.Y., chapters 5-8 and 15, ISBN 0-87969-314-2.

The phrase "human engineered antibodies" refers to monoclonal antibodies that have binding and functional properties according to the invention, and that have framework regions that are substantially human or fully human surrounding CDRs derived from a non-human antibody. "Antigen-binding fragments" of such human engineered antibodies include, for example, Fab fragments, Fab' fragments, F(ab')₂ fragments, and single chain Fv fragments. "Framework region" or "framework sequence" refers to any one of framework regions 1 to 4. Human engineered antibodies and antigen-binding fragments thereof encompassed by the present invention include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, about 95%, or about 99% sequence identity to a known human germline framework sequence.

Fully human frameworks are those that are identical to a known human germline framework sequence. Human framework germline sequences can be obtained from ImMunoGeneTics (IMGT) via their website http://imgt.cines.fr, or from *The Immunoglobulin FactsBook* by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L11, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Human engineered antibodies in addition to those disclosed herein exhibiting similar functional properties according to the present invention can be generated using several different methods. The specific antibody compounds disclosed herein can be used as templates or parent antibody compounds to prepare additional antibody compounds. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816, 397; 5,225,539, and 5,693,761; computer programs ABMOD and ENCAD as described in Levitt (1983) *J. Mol. Biol.* 168: 595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows:

When an amino acid falls under the following category, the framework amino acid of the human germ-line sequence that is being used (the "acceptor framework") is replaced by a framework amino acid from a framework of the parent antibody compound (the "donor framework"):

(a) the amino acid in the human framework region of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) *J. Mol. Biol.* 294:151-162.

Applying the teachings of the present invention, a person skilled in the art can use common techniques, e.g., site-directed mutagenesis, to substitute amino acids within the presently disclosed CDR and framework sequences and thereby generate further variable region amino acid sequences derived from the present sequences. All alternative naturally occurring amino acids can be introduced at a specific substitution site. The methods disclosed herein can then be used to screen these additional variable region amino acid sequences to identify sequences having the indicated in vivo functions. In this way, further sequences suitable for preparing human engineered antibodies and antigen-binding portions thereof in accordance with the present invention can be identified.

Preferably, amino acid substitution within the frameworks is restricted to one, two, or three positions within any one or more of the 4 light chain and/or heavy chain framework regions disclosed herein. Preferably, amino acid substitution within the CDRs is restricted to one, two, or three positions within any one or more of the 3 light chain and/or heavy chain CDRs. Combinations of the various changes within these framework regions and CDRs described above are also possible.

The term "treating" (or "treat" or "treatment") refers to processes involving a slowing, interrupting, arresting, controlling, stopping, reducing, or reversing the progression or severity of an existing symptom, disorder, condition, or disease, but does not necessarily involve a total elimination of all disease-related symptoms, conditions, or disorders associated with the anti-N3pGlu Aβ antibody.

The antibodies of the present invention can be used as medicaments in human medicine, administered by a variety of routes. Most preferably, such compositions are for parenteral administration. Such pharmaceutical compositions can be prepared by methods well known in the art (See, e.g., *Remington: The Science and Practice of Pharmacy*, $19^{th}$ ed. (1995), A. Gennaro et al., Mack Publishing Co.) and comprise an antibody as disclosed herein or an antigen-binding fragment thereof, and a pharmaceutically acceptable carrier, diluent, or excipient.

The results of the following assays demonstrate that the monoclonal antibodies and antigen-binding fragments thereof of the present invention are useful for treating a condition associated with Aβ peptide activity such as Alzheimer's disease, Down's syndrome, and CAA.

EXAMPLE 1

Production of Antibodies

Initial Antibody Generation:

FVB transgenic mice are immunized with the N-terminal truncated and pyroglutamate-modified human amyloid β peptide 3-42 (N3pGlu) pretreated at 37° C. overnight to form aggregate. Mice spleen cells are harvested and Aβ1-40 reactive B cells depleted by MACS. Remaining cells are sorted for binding to aggregated N3pGlu Aβ peptide. RNA is isolated from the selected B-cells and converted into cDNA using oligo dT. Antibody heavy and light chain variable regions are obtained by PCR using antibody signal sequence primers and cloned into phage vector by Kunkel mutagenesis to make the Fab library. The Fab library is screened for binding to the aggregated N3pGlu peptide by Single-Point ELISA (SPE) and counter-screened against Aβ1-40. Positive clones are characterized by DNA sequencing, fab expression, and binding to the N3pGlu Aβ peptide, and lack of binding to soluble Aβ1-40 or Aβ1-42 peptide.

Single amino acid mutant libraries are constructed and screened by SPE for binding to aggregated N3pGlu Aβ peptide, but not to Aβ1-42. Beneficial mutations are combined into combinatorial libraries. The affinity-optimized combinatorial variants are selected and converted into mouse IgG1 for affinity measurement by BIACORE® and Aβ plaque binding by immunohistochemistry. From an identified clone, mAb protein is made in both mouse IgG1 (mE8) and IgG2a (mE8c) isotypes for in vivo efficacy studies. mE8 does not bind to mouse N3pGlu Aβ sequence (mpE3-16) or human Aβ1-42.

Human germline frameworks VH1-69/JH6 and Vk-A18/JK2 are used for the initial humanization. CDRs of mE8 antibody (with four affinity mutations) are grafted into the human frameworks resulting in antibody hE8-C6. Further affinity optimization is carried out on hE8-C6 backbone, and beneficial mutations are combined to make the high affinity, humanized variant R5, R17, R24 and 2420.

Second Round of Optimization to Improve Drug Developability:

Two humanized variants, hE8-C6 and R17, are chosen as backbone for a second round of optimization to improve antibody serum half life by reducing non-specific binding to cells and to increase antibody affinity to soluble N3pGlu Aβ peptide. A biotinylated soluble peptide consisting of the N-terminal 14 amino acid of N3pGlu Aβ (pE3-16B) is synthesized and evaluated to be equivalent to N3pGlu Aβ peptide for antibody mE8 binding. A high-throughput filter life assay using pE3-16B is developed and applied to all subsequent library screening. All hits from filter lift screen are confirmed by binding to aggregated N3pGlu Aβ.

Libraries of hE8-C6 variants are re-screened using the filter lift assay and a set of beneficial mutations are identified. A subset of them is used to make the combinatorial library. Four combi variants (CoII-E10, CoII-G2, CoII-G8 and CoII-E2) are selected from this approach.

Computer modeling is employed to create V-region structural models of hE8-C6, R17, R24 and other variants. Structural model analysis identifies positive charges introduced for affinity optimization clustering in the binding site, a potential cause of antibody non-specific binding to cells. Based on the modeling, several positions are selected for introducing changes to balance the surface electrostatic potential. A combinatorial library is synthesized by combining some beneficial mutations from library screening and the changes defined by structural modeling. Three variants (R17m-B4, R17m-A12 and R17m-B12) are selected from this effort for further studies.

Structural model analysis also discovers a steric clash between the light chain framework residue Y36 and residues in the heavy chain CDR3. Mutation Y36L is introduced to hE8-C6 light chain to produce variant hE8L. This framework change alone is found to have significant impact on both increasing antibody affinity and reducing non-specific cell binding.

The other effort was to test different human framework for the humanization. CDRs of mE8 antibody are grafted on frameworks VH5-51/VKO2 and VH3-23/VKA2. The humanized Fab with VII5-51/VKO2 (hE8-51O2) is determined as equivalent, if not better, to hE8-C6 in N3pGlu Aβ binding. Introduction of additional beneficial mutations into hE8-51O2 generates combi variants CI-A1, CI-B6, CI-C7 and CI-B8.

After passing all in vitro assays, including ELISA and BIACORE® for antigen specificity and affinity, non-specific cell binding, and IIIC staining, five variant mAbs, B12L, CI-C7, hE8L, R17L, and R17 are selected.

Antibodies can be made and purified essentially as follows. An appropriate host cell, such as HEK 293 EBNA or CHO, is either transiently or stably transfected with an expression system for secreting antibodies using an optimal predetermined HC:LC vector ratio or a single vector system encoding both HC, such as SEQ ID NO: 56, and SEQ ID NO: 43, and LC, such as SEQ ID NO: 55. Clarified media, into which the antibody has been secreted, is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized. The amino acid sequences for these antibodies of the present invention are provided below.

TABLE 1

| Antibody SEQ ID NOs | | | | |
|---|---|---|---|---|
| Antibody | Light Chain | Heavy Chain | LCVR | HCVR |
| I (B12L) | 14 | 15 | 11 | 12 |
| II (R17L) | 14 | 16 | 11 | 13 |
| III (hE8L) | 14 | 44 | 11 | 42 |
| IV (R17) | 38 | 16 | 36 | 13 |
| V (CI-C7) | 49 | 50 | 47 | 48 |
| VI (mE8) | 22 | 23 | 20 | 21 |
| VII (mE8c) | 22 | 24 | | |

EXAMPLE 2

Binding Affinity to Soluble N3pGlu

Surface plasmon resonance measured with the BIACORE® 2000 instrument is used to measure binding of N3pGlu Aβ to anti-N3pGlu antibodies. Except as noted, all reagents and materials are from BIACORE® AB (Upsala, Sweden). All measurements are performed at 25° C. Samples are dissolved in HBS-EP buffer (150 mM sodium chloride, 3 mM EDTA, 0.005% (w/v) surfactant P-20, and 10 mM HEPES, pH 7.4).

A series of Abeta peptides with positional changes (glycine mutants) are synthesized to assess the impact of a given residue on antibody binding and thereby identify the characteristics and the sequence required for antibody recognition:

```
Peptide name   Abeta 3-16 Sequence pE3-16         Pyr-EFRHDSGYEVHHQK-biotin              SEQ ID NO: 25

E3-16          EFRHDSGYEVHHQK-biotin                  SEQ ID NO: 26 pEG4           Pyr-EGRHDSGYEVHHQK-biotin              SEQ ID NO: 27 mpE3-16        Pyr-EFGHDSGFEVHHQK-biotin (rodent)     SEQ ID NO: 28 pEG6           Pyr-EFRGDSGYEVHHQK-biotin              SEQ ID NO: 29
```

-continued

| Peptide name | Abeta 3-16 Sequence | |
|---|---|---|
| pEG7 | Pyr-EFRHGSGYEVHHQK-biotin | SEQ ID NO: 30 |
| pEG8 | Pyr-EFRHDGGYEVHHQK-biotin | SEQ ID NO: 37 |
| pEF10 | Pyr-EFRHDSGFEVHHQK-biotin | SEQ ID NO: 39 |

The importance of a truncated (des 1,2) and modified form of glutamic acid (3 pyr-E or 3 pyr-Glu) is assessed by comparing Aβ1-42 binding versus Aη3-16 versus pE3-16 (SEQ ID NO:1 versus SEQ ID NO:26 versus SEQ ID NO:25, respectively). Peptides are dissolved in PBS at 5 mg/ml prior to dilution for binding experiments.

Binding is evaluated using multiple analytical cycles of antibody capture, peptide injection/association, prolonged buffer flow for dissociation, and surface regeneration. For the antibody capture step, depending on the type of antibody to be captured, a CM5 chip is immobilized with either protein A or goat anti-mouse Fc. Except for mouse antibodies, each cycle consists of: injection of ~5-7 µL of 10 µg/mL anti-N3pGlu antibody at 5 µl/min (capture app. 3,000 RU), injection of 100 µL of peptide at 50 µl/min (1000 nM-62.5 nM in two-fold serial dilutions for each cycle), followed by 10 minutes for dissociation. For a mouse antibody, the flow rate is 50 µL/min, and 20 µL of mouse antibody at 50 m/ml is injected. In both cases, the chip surface is regenerated using 20 µL of 10 mM glycine hydrochloride, pH 1.5. The binding affinity ($K_D$) is then obtained from association and dissociation rates for each cycle using a 1:1 binding model in the BIAevaluation analysis software. The anti-N3pGlu antibodies, B12L and R17L and the parental mouse antibody (mE8C) recognize N3pGlu Aβ specifically, with a $K_D$ less than 1 nM. Anti-N3pGlu antibodies, B12L and R17L and parental mouse antibody (mE8C) also bind to pE3-16 with similar affinity, indicating the epitope is located within this region of the peptides. Binding analysis of antibodies to glycine mutant peptides shows that the residues critical for binding were from 3 to 7: pyroE at position 3, F at position 4, R at position 5, H at position 6, D at position 7. Detectable binding to $Aβ_{1-40}$ is not detected for the antibodies of the present invention.

EXAMPLE 3

Binding Affinity to Aggregated N3pGlu

BIACORE® experiments are also conducted to monitor the binding of anti-N3pGlu antibodies to aggregated N3pGlu Aβ. In this experiment, N3pGlu Aβ peptide is immobilized at different densities to flow cells 2 (low density, LD), 3 (medium density, MD), and 4 (high density, HD) on a CM-5 chip through amine coupling chemistry. Different levels of N3pGluAβ peptide are immobilized to examine the impact of surface density on binding of anti-N3pGlu antibodies. Upon immobilization, the majority of N3pGluAβ aggregates on the surface as demonstrated by the lack of the binding of a control Mab which only recognizes the monomeric peptide. This aggregated form of peptide mimics the property of aggregated abeta peptide in fibril or amyloid form, where the N-terminal region of the peptides is exposed and can be targeted with antibodies.

Binding is evaluated using multiple analytical cycles at 25° C. Each cycle is performed at a flow rate of 50 µL/min and consists of the following steps: injection of 250 µL of N3pGlu antibody solution (starting at 500 nM and using two-fold serial dilutions for each cycle) followed by 20 minutes for dissociation, and regeneration using ~30 µL of 10 mM glycine hydrochloride, pH 1.5. Association and dissociation rates for each cycle are evaluated using a heterogeneous ligand model in the BIAevaluation software. Since 1:1 binding model does not fit the data, the heterogeneous fit yields two binding affinities (a low and a high affinity). The R17L and B12L antibodies and parental murine antibody mE8c bind to aggregated N3pGlu Aβ with high affinity $K_{D,1}$<100 pM and a lower affinity $K_{D,2}$<10 nM. The maximum binding signal (Rmax) was calculated as the sum of Rmax from low and high affinity binding. The Rmax is shown to increase as the density of the peptide on the surface increased, as expected when more binding sites are available at higher density surface. These binding studies demonstrate that antibodies of the present invention bind to aggregated N3pGlu Aβ.

EXAMPLE 4

Ex Vivo Target Engagement Studies

Immunohistochemical analysis is performed with exogenously added Aβ antibodies in order to determine ex vivo target engagement on brain sections from a fixed PDAPP brain (24-month old). The PDAPP transgenic mouse has been shown to develop much of the pathology associated with Alzheimer's disease. For murine antibodies, a biotin tag was used as the label since this experiment was conducted on murine tissue, and thus a direct comparison between the non-biotinylated non-murine anti-N3pGlu antibodies is not appropriate. The biotinylated 3D6 N terminal (1-5) antibody robustly labels significant quantities of deposited Aβ in the PDAPP hippocampus, whereas the biotinylated mE8 labels only a subset of deposits. Unlike the human AD brain, the vast majority of deposited Aβ in PDAPP brain is full length. A similar plaque labeling for the non-biotinylated anti-N3pGlu antibodies, such as B12L and R17L (compared to the mE8), is observed. No specific plaque labeling is observed for either the mouse or human control IgG's. Because the composition and likely structure of the deposited Aβ is dramatically different in AD brain, the non-biotinylated anti-N3pGlu (3 ug/ml) antibodies are investigated to determine whether they bind deposited Aβ on brain sections from a freshly-frozen AD brain. The positive control antibody (biotinylated 3D6) intensely labels many Aβ plaques in the AD brain, whereas the negative control antibodies (murine and human IgG) lacks any appreciable binding. Several of the non-biotinylated anti-N3pGlu antibodies such as B12L and R17L bind similarly to the deposited Aβ. These histological studies demonstrate that the anti-N3pGlu antibodies of the present invention can engage the deposited Aβ target ex vivo.

EXAMPLE 5

In Vivo Target Engagement Studies

The ability of the anti-N3pGlu antibodies to engage the deposited target in vivo is measured. A sub-chronic 4-week study is performed with biotinylated murine antibodies 3D6 and mE8c at 40 mg/kg administered intraperitoneally (IP) weekly. Brains are harvested at the conclusion of the experiment and the level of target engagement is determined by histological examination of the brain. The animals injected with the biotinylated 3D6 have plaque labeling only along the hippocampal fissure, whereas mice injected with biotinylated mE8c display robust plaque labeling in the hippocampus and cortical regions. Very similar target engagement patterns are observed in a more acute 3-day assay (3D6 hippocampal fissure staining and mE8 labeling both hippocampal and cortical regions). These results strongly suggest that the 3D6 antibody, which binds both soluble and insoluble Aβ, is becoming saturated with soluble Aβ and thus is not able to engage the desired deposited target. In stark contrast, the murine anti-N3pGlu antibody mE8c consistently engages the intended target in both of the critical brain regions. High and low doses of the R17L and B12L anti-N3pGlu antibodies are evaluated in a similar 3-day in vivo study. The antibodies are injected IP at either 10 mg/kg (low dose) or 40 mg/kg (high dose). At the conclusion of the study, plasma and brains are harvested and plasma PK determined. The brains are sectioned and immunohistochemistry is performed on sister sections with an anti-human antibody (to detect the bound anti-N3pGlu antibody) and 3D6 (to detect the total amount of deposited target in the section). In order to better quantify the level of in vivo target engagement, the percent area bound by the anti-N3pGlu antibody is normalized against the total % area of possible target (total deposited Aβ visualized by exogenous 3D6 immunohistochemistry). Additionally, the overall percent target engagement is normalized against the plasma pharmacokinetics (PK) values for each individual mouse since significant exposures are detected at the conclusion of the study. Both the R17L and B12L anti-N3pGlu antibodies are found to engage the deposited plaque with a similar distribution as that observed with the murine anti-N3pGlu antibody (mE8). These results demonstrate that the R17L and B12L anti-N3pGlu antibodies when administered peripherally can cross the blood-brain barrier and engage the intended target of deposited Aβ, whereas an antibody that binds both soluble and insoluble Aβ becomes saturated with the soluble and cannot engage the intended deposited target.

EXAMPLE 6

Therapeutic Plaque Lowering Studies

A therapeutic plaque lowering study in 23-month old PDAPP mice is performed with the following antibodies: negative control antibody (IgG2a), 3D6, mE8 (IgG1), and mE8c (IgG2a). The aged PDAPP mice are injected subcutaneously with 12.5 mg/kg of each antibody weekly for three months. A group of mice is necropsied at the beginning of the study (time zero) in order to determine the initial plaque load at 23-months of age. At the conclusion of the study, plasma is obtained and the brains are processed for biochemical and histological outcomes (one hemi-brain each). The hippocampus and cortical regions are homogenized in 5M guanidine and the Aβ content measured by acid urea gels followed by Western blotting. An analysis of the hippocampal guanidine lysates from the 23-month old time zero and negative antibody control (26-month old) cohorts show a non-significant increase in deposited $A\beta_{1-42}$; thereby confirming that the brains of the PDAPP mice are at the plaque plateau. Similar to previous studies in aged PDAPP mice, treatment with the comparator antibody 3D6 has no effect on plaque lowering. The treatment with either N3pGlu antibody, mE8 or mE8c, results in significant plaque lowering as compared to the IgG2a negative control antibody (p<0.01 and p<0.001, respectively)(Table 2). The mE8 and mE8c lowers the hippocampal $A\beta_{1-42}$ by ~38% and ~53%, respectively. The N3pGlu antibody mE8c with maximal effector function trends to being more efficacious than the minimal effector function antibody mE8 (compared to control), however this difference does not reach statistical significance. Also, the mE8c antibody has a significant ~30% lowering of $A\beta_{1-42}$ in the hippocampus as compared to the time zero mice (t-test; p<0.0066), thus indicating clearance of previously deposited plaque. The analyses of the cortical guanidine lysates yield very similar outcomes with the exception that only the mE8c with maximal effector function significantly decreases $A\beta_{1-42}$ deposition. These results demonstrate that chronic treatment with N3pGlu antibodies of this Example significantly decreases plaque deposition in aged PDAPP mice in an effector function dependent manner. Additionally, these results support the hypothesis that poor target engagement for Aβ antibodies that bind both soluble and insoluble Aβ (as opposed to senescence) was the causative factor for their lack of efficacy when used in therapeutic paradigms.

TABLE 2

Hippocampal and Cortex plaque lowering
(ng $A\beta_{1-42}$/mg wet weight)

|  | Time Zero Control | Negative Control - IgG2a | m3D6 | mE8 - IgG1 | mE8c - IgG2a |
|---|---|---|---|---|---|
| Hippocampal plaque of 23 to 26-month old PDAPP mice | | | | | |
| Number of values | 15 | 27 | 30 | 27 | 23 |
| Mean | 48.13 | 71.96 | 66.73 | 44.25 | 33.62 |
| Std. Deviation | 17.12 | 39.4 | 29.48 | 19.64 | 13.8 |
| Std. Error | 4.42 | 7.583 | 5.383 | 3.78 | 2.877 |
| Cortex plaque of 23 to 26-month old PDAPP mice | | | | | |
| Number of values | 15 | 27 | 30 | 27 | 24 |
| Mean | 34.43 | 41.93 | 40.46 | 33.66 | 27.52 |
| Std. Deviation | 16.14 | 19.98 | 18.14 | 14.91 | 16.95 |
| Std. Error | 4.168 | 3.845 | 3.313 | 2.869 | 3.459 |

EXAMPLE 7

Analysis of Microhemorrhage in Aged PDAPP Mice

A histological study is performed to investigate whether the mechanism of action of the N3pGlu antibodies that leads to decreased plaque lowering in aged PDAPP mice would result in an exacerbation of CAA-related microhemorrhage. Previous studies have demonstrated that treatment of aged APP transgenic mice with certain anti-Aβ amino-terminal and carboxyl-terminal antibodies will lead to an increase in CAA-related microhemorrhage (Pfeifer et al. 2002; Wilcock et al. 2004; Racke et al. 2005). Although the mechanism underlying this potential adverse event is unclear, two non-mutually exclusive hypotheses have been proposed: the redistribution of Aβ into the cerebral blood vessels (Wilcock et al. 2004) or the direct binding of antibodies to existing CAA (Racke et al. 2005). Biochemical and histological analyses demonstrate that $A\beta_{p3-x}$ is a constituent of CAA in both AD patients and aged PDAPP mice. A detailed histological analysis for microhemorrhage in aged PDAPP mice (23 to 26 months of age) that have been therapeutically treated with N3pGlu and control antibodies is performed for three months with weekly subcutaneously injections of 12.5 mg/kg. The positive control for the microhemorrhage analyses is the 3D6 chronically treated animals which have previously demonstrated that this anti-Aβ amino-terminal antibody significantly exacerbates microhemorrhage (Racke et al. 2005). At the conclusion of the study, one hemi-brain from each animal is drop-fixed in 4% formaldehyde and imbedded in paraffin. Coronal sections encompassing 2 mm of tissue are sectioned on to 50 slides (four 10 μm sections per slide). Eleven slides from even intervals across the 2 mm of tissue are stained with Perls Blue in order to visualize hemosiderin (cellular iron accumulation due to microhemorrhage). Two sections per slide are manually counted in a blinded fashion. Chronic treatment of aged PDAPP mice with 3D6 (positive control) dramatically increases microhemorrhage ($p<0.001$). Importantly, it is demonstrated that treatment with either mE8 (IgG1) or mE8c (IgG2a) does not exacerbate microhemorrhage, even though these N3pGlu antibodies significantly lower deposited Aβ in these animals. These results demonstrate that the N3pGlu antibodies of this Example do not exacerbate CAA-related microhemorrhage in aged PDAPP mice.

We claim:

1. A human engineered anti-N3pGlu Aβ antibody comprising a Light chain Variable Region (LCVR) and a Heavy chain Variable Region (HCVR) wherein LCDR1 is KSX1X2SLLYSRX3KTYLN (SEQ ID NO: 51), LCDR2 is AVSKLX4S (SEQ ID NO: 52), LCDR3 is VQGTHYPFT (SEQ ID NO: 5) and HCDR1 is GYX5FTX6YYIN (SEQ ID NO: 53), HCDR2 is WINPGSGNTKYNEKFKG (SEQ ID NO: 8), and HCDR3 is EGX7TVY (SEQ ID NO: 54), wherein X1 is S or T; X2 is Q or R, X3 is G or S, X4 is D or G, X5 is D or T, X6 is R or D, and X7 is I, T, E, or V.

2. The human engineered anti-N3pGlu Aβ antibody of claim 1, wherein the LCVR framework is substantially human VK02 light chain germ line sequence and the HCVR framework is substantially human VH5-51 heavy chain germ line sequence.

3. A pharmaceutical composition comprising the human engineered antibody of claim 1, and a pharmaceutically acceptable carrier, diluent, or excipient.

4. A pharmaceutical composition comprising the human engineered antibody of claim 2, and a pharmaceutically acceptable carrier, diluent, or excipient.

5. A method of treating a condition selected from the group consisting of clinical or pre-clinical Alzheimer's disease, prodromal Alzheimer's disease, Down's syndrome, and clinical or pre-clinical cerebral amyloid angiopathy (CAA), comprising administering to a human in need thereof the human engineered antibody of claim 1.

6. A method of treating a condition selected from the group consisting of clinical or pre-clinical Alzheimer's disease, prodromal Alzheimer's disease, Down's syndrome, and clinical or pre-clinical cerebral amyloid angiopathy (CAA), comprising administering to a human in need thereof the human engineered antibody of claim 2.

7. A method of treating a condition selected from the group consisting of clinical or pre-clinical Alzheimer's disease, prodromal Alzheimer's disease, Down's syndrome, and clinical or pre-clinical cerebral amyloid angiopathy (CAA), comprising administering to a human in need thereof the pharmaceutical composition of claim 3.

8. A method of treating a condition selected from the group consisting of clinical or pre-clinical Alzheimer's disease, prodromal Alzheimer's disease, Down's syndrome, and clinical or pre-clinical cerebral amyloid angiopathy (CAA), comprising administering to a human in need thereof the pharmaceutical composition of claim 4.

9. A method of treating Alzheimer's disease, comprising administering to a human in need thereof the human engineered antibody of claim 1.

10. A method of treating Alzheimer's disease, comprising administering to a human in need thereof the human engineered antibody of claim 1.

11. A method of treating Alzheimer's disease, comprising administering to a human in need thereof the pharmaceutical composition of claim 3.

12. A method of treating Alzheimer's disease, comprising administering to a human in need thereof the pharmaceutical composition of claim 4.

* * * * *

UNITED STATES PATENT AND TRADEMARK OFFICE
CERTIFICATE OF CORRECTION

| | | |
|---|---|---|
| PATENT NO. | : 8,961,972 B2 | Page 1 of 1 |
| APPLICATION NO. | : 14/039113 | |
| DATED | : February 24, 2015 | |
| INVENTOR(S) | : Jirong Lu et al. | |

It is certified that error appears in the above-identified patent and that said Letters Patent is hereby corrected as shown below:

On the Title Page, item (56), reference 7 by author Margaret M. Racke, et al. under the "OTHER PUBLICATIONS" section, please delete "Socitey" and insert --Society--, therefor.

In the Claims,

Column 69, line 54, claim 1, delete "Light chain" and insert --Light Chain--, therefor.

Column 69, line 54, claim 1, delete "Heavy chain" and insert --Heavy Chain--, therefor.

Column 71, line 21, claim 10, delete dependency to "claim 1" and insert --claim 2--, therefor.

Signed and Sealed this
Seventh Day of June, 2016

Michelle K. Lee
*Director of the United States Patent and Trademark Office*